United States Patent [19]
Derkacs et al.

[11] Patent Number: 4,523,468
[45] Date of Patent: Jun. 18, 1985

[54] PHASED ARRAY INSPECTION OF CYLINDRICAL OBJECTS

[75] Inventors: Thomas Derkacs, Mayfield Village; Istvan M. Matay, North Royalton; Stephan D. Murphy, East Cleveland; John Touhalisky, Eastlake, all of Ohio

[73] Assignee: TRW Inc., Cleveland, Ohio

[21] Appl. No.: 538,627

[22] Filed: Oct. 3, 1983

[51] Int. Cl.³ ............................................. G01N 29/04
[52] U.S. Cl. ...................................... 73/598; 73/622; 73/626; 73/628
[58] Field of Search ................ 73/597, 598, 600, 620, 73/622, 625, 626, 628, 637, 638, 640, 641

[56] References Cited

U.S. PATENT DOCUMENTS 4,160,386 7/1979 Jackson et al. ........................ 73/622
4,354,388 10/1982 Diepers et al. ........................ 73/628

OTHER PUBLICATIONS

H. Seiger, "Comparison of Three Flaw-Location Methods for Automated Ultrasonic Testing", *NDT International*, pp. 131-135, Jun. 1982.

*Primary Examiner*—Stephen A. Kreitman
*Attorney, Agent, or Firm*—Daniel G. Blackhurst

[57] ABSTRACT

A first array (A) of ultrasonic transducers transmits ultrasonic shear waves circumferentially around an examined cylindrical object (110). A second array (B) transmits ultrasonic shear waves axially along the examined object. Triggering pulses from a triggering amplifier (22) are switched by a multiplexer (24) to each individual transducer of the first and second arrays. As one of the transducers assumes the role of a transmitting transducer and transmits an ultrasonic wave, the other transducers of the first and second arrays assume a receiving mode to receive reflected ultrasonic components. A wave travel timer (26) measures the duration for an ultrasonic wave to be transmitted from the transmitting transducer to a defect and for a reflected component to propagate from the defect to the receiving transducer. A microprocessor (20) tri-angulates or otherwise computes the location and orientation of a reflective defect from the measured travel time, the spatial relationship of the transmitting and receiving transducers, and the direction of propagation of the transmitted ultrasonic wave.

16 Claims, 5 Drawing Figures

PHASED ARRAY INSPECTION OF CYLINDRICAL OBJECTS

BACKGROUND OF THE INVENTION

The present invention relates to the art of acoustical defect detection. The present invention finds particular application in the ultrasonic inspection of cylindrical objects such as metal pipe and tubing, and will be described with particular reference thereto. It is to be appreciated, however, that the invention has other applications including acoustical examination of sheet materials, polygonal members, rods, and the like.

Heretofore, ultrasonic transducers have been utilized in a pulse-echo mode to locate flaws and defects in an examined object. In the pulse-echo mode, an ultrasonic transducer is first caused to transmit an ultrasonic wave and then waits to receive an echo from a defect. The angle of incidence and angle of reflection relative to the surface of the defect must be equal. Thus, a transmitting transducer can only receive an echo from a defect surface which is substantially normal to the direction of ultrasonic wave transmission. Defect surfaces which are more than 5° off-normal to the direction of propagation reflect the ultrasonic wave, but do not return a sufficiently large component to the transmitting transducer for the defect to be detected.

Ultrasonic transducers have been used in a pulse-echo mode to generate ultrasonic shear waves traveling peripherally around the examined object, and to detect echoes reflected peripherally back to the transducer. Axially oriented ultrasonic transducers have been used to generate axial shear waves and detect axial echoes. Similarly, ultrasonic transducers have been oriented perpendicular to the examined surface and operated in a pulse-echo mode. Further, others have oscillated or rocked the transducers to examine the object from a multiplicity of angles.

A three dimensional defect commonly has at least some surface portion which is normal to one of the pulse-echo operated transducers and is readily detected. However, a two dimensional defect, such as a crack, can only be detected by pulse-echo transducers which are oriented substantially perpendicular to the surface of the crack. Thus, peripherally oriented pulse-echo transducers and axially oriented pulse-echo transducers are only able to detect cracks which are substantially parallel or perpendicular to the axis.

It has been suggested to have ultrasonic transducers propagate ultrasonic waves around the examined object in a spiral at various angles, eg., 45°. However, because the direction of propagation must be within 5° of normal to a crack to be assured of detection, a wide range of wave propagation directions would be required for assuring that cracks would not go undetected.

The present invention contemplates an arrangement which overcomes the above referenced problems and others, and provides an ultrasonic inspection system which detects defects and cracks oriented at a wide variety of orientations in an examined object.

SUMMARY OF THE INVENTION

In accordance with the present invention, there is provided a method of ultrasonically locating defects in an examined object with first and second transducer arrays. The first transducer array is disposed for transmitting and receiving ultrasonic waves propagating in a first direction, and the second array disposed for transmitting and receiving ultrasonic waves propagating in a second direction. The transducers in the first transducer array are actuated individually or in small groups to transmit an ultrasonic wave. The transducers in both arrays are operated in a receive mode to receive ultrasonic echoes. The travel time between transmission of the wave and receipt of an echo is measured. From the wave transmission direction, travel time, and the spatial relationship of the transmitting and receiving transducers, the location of a reflective defect is tri-angulated or otherwise determined. This process is repeated with each transducer in the first and second arrays operated in its transmission mode.

In accordance with another aspect of the invention, an ultrasonic defect detection apparatus is provided. A first transducer array, including a plurality of first transducers, is disposed for transmitting ultrasonic shear waves along the examined object in a first direction. A second transducer array including a plurality of second transducers is disposed to transmit ultrasonic shear waves along the object in a second direction. A multiplexing means selectively switches triggering pulses to each transducer of the first and second ultrasonic transducer arrays. After each transmission, the first and second ultrasonic transducer arrays assume a receiving mode. An ultrasonic wave travel time measuring means measures the time between transmission of the ultrasonic wave and receipt of an echo. A defect location determining means determines the location of a reflective defect from the wave transmission direction, the determined travel time, and the spatial relationship of the transmitting and receiving transducers.

A primary advantage of the present invention is the detection of two dimensional defects and cracks having substantially any orientation.

Another advantage of the invention resides in the capability to examine an object for defects relatively quickly and accurately.

Still another advantage of the invention is found in the accurate location and determination of defect dimensions.

Still other advantages and benefits of the present invention will become apparent to those of ordinary skill in the art upon reading and understanding the following detailed description.

BRIEF DESCRIPTION OF THE DRAWINGS

The invention may take form in various steps and arrangements of steps and in various parts and arrangements of parts, preferred and alternative embodiments of which will be described in detail in the following specification and illustrated in the accompanying drawings which form a part hereof and wherein.

DETAILED DESCRIPTION OF THE PREFERRED EMBODIMENT

Figure 1:
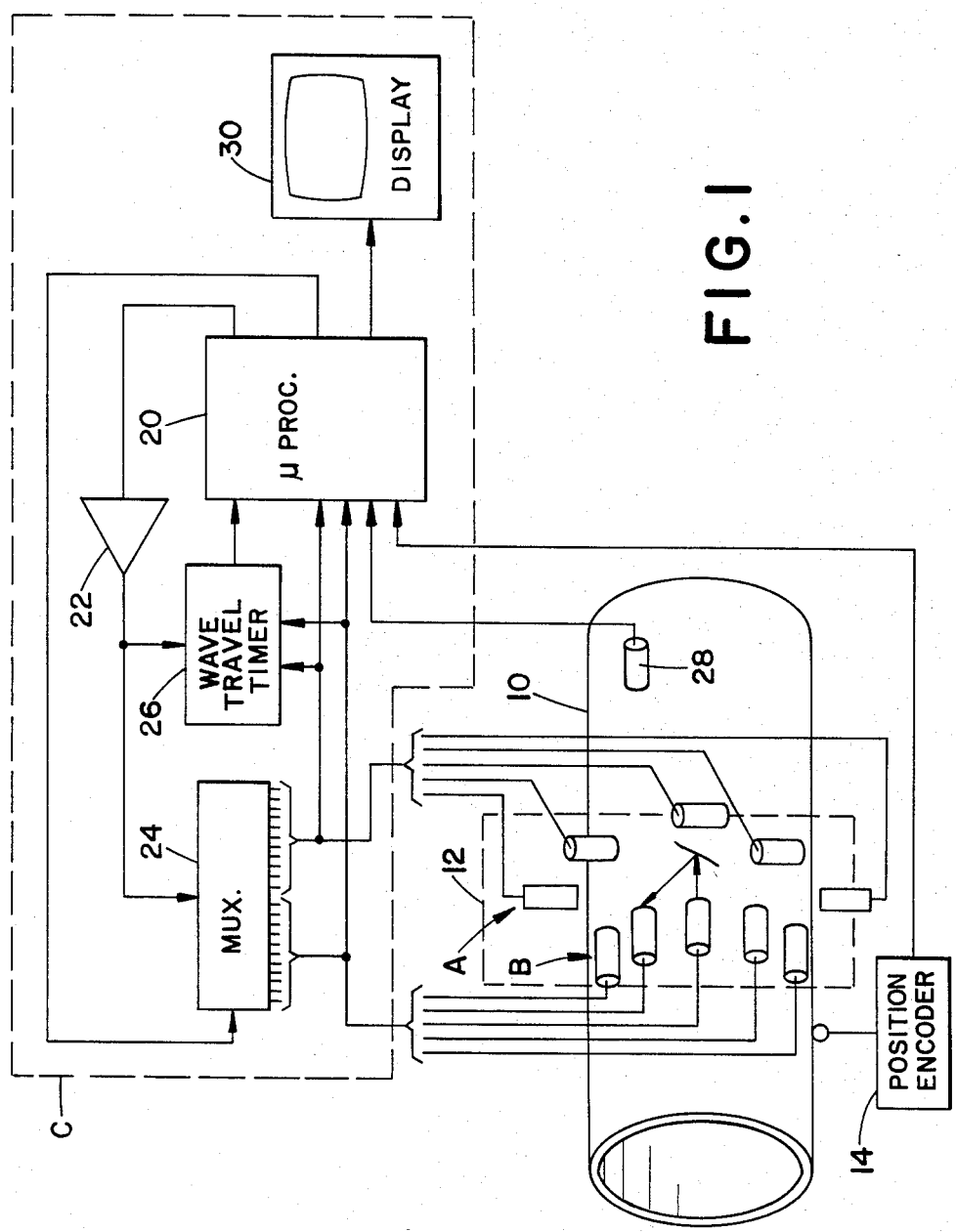
FIG. 1 is a diagrammatic illustration of a microprocessor based apparatus for detecting defects in accordance with the present invention.

With reference to the drawings wherein the showings are for purposes of illustrating preferred and alternative embodiments of the invention only and not for purposes of limiting same, each transducer of a first transducer array A in FIG. 1 is oriented so as to transmit ultrasonic waves propagating along an examined object in a first direction. Each transducer of a second transducer array B is oriented to generate ultrasonic waves propagating in a second direction.

In the preferred embodiment, the first and second directions are orthogonal to the circumferential direction. The use of orthogonal propagation directions simplifies the algorithm for determining the position at which a flaw is located, but is not required. An electronic circuit C selectively actuates or triggers transducers of the first and second arrays to generate ultrasonic waves propagating in the first and second directions, causes the transducers of the first and second arrays to assume an echo receiving mode, and determines the size, location, orientation, and other physical characteristics of cracks and defects.

In the preferred embodiment, the examined object comprises a cylindrical steel pipe or tube 10. The transducers of the first ultrasonic array A are disposed to propagate ultrasonic waves through a coupling medium in a collar 12 to the examined object. The transducers of the first array are oriented such that shear waves are propagated circumferentially around the examined object. The transducers of the second array are oriented to transmit ultrasonic waves through the coupling medium to propagate ultrasonic shear waves axially along the examined object. In the preferred embodiment, the first and second transducer arrays are disposed circumferentially or peripherally around the entirety of the object. Alternately, the first and second arrays may extend only partially around the examined object, and the examined object may be rotated to bring all portions thereof into association with the transducer arrays. As the object 10 is relatively moved axially through the first and second arrays, A, B, a position encoder 14 produces electronic signals indicative of the location of the arrays relative to an arbitrary point or origin of the object.

A microprocessor 20 periodically enables or actuates a triggering means 22 causing it to produce an ultrasonic transducer trigger pulse. A multiplexing means 24 switches the triggering pulse to a selected ultrasonic transducer of the first and second arrays. The microprocessor controls the multiplexing means such that the multiplexing means selectively switches trigger pulses serially to each of the transducers in the first and second arrays. An ultrasonic wave travel timer 26 measures the time interval between transmission of an ultrasonic wave and receipt of an ultrasonic echo. Although illustrated as a separate component connected with the triggering means and with the transducers of the first and second arrays, the wave travel timing means may comprise an integral part of the microprocessor 20. Optionally, one or more transducers 28 may be disposed a preselected distance from one of the axial transducers to measure the velocity of the ultrasonic shear waves in the examined object.

The microprocessor is programmed to calculate the location of each defect which produces a received ultrasonic echo and display the defect location on a display means 30. In this manner, the microprocessor functions as a location determining means which determines defect locations from the spatial relationship of the transmitting and receiving transducers, the direction of transmission of the ultrasonic wave, and the travel time. In addition, the microprocessor determines and displays other characteristics of each defect, such as the orientation of the reflecting surface, the reflectivity of the defect, and the like.

The location of the flaws is calculated using a form of triangulation. It is to be appreciated that the transmitting transducer, the defect, and the receiving transducer define the three corners of a triangle. The spatial relationship of the transducers determines the length of one side of the triangle, ie., the distance between the transmitting and receiving transducers. The direction of propagation determines the angle between the sides of the triangle which meet at the transmitting transducer. The wave travel time in conjunction with a premeasured propagation speed provides an indication of the sum of the length of the other two sides of the triangle. From this data, the location and angular orientation of a defect relative to the transmitting transducer may be calculated.

Figure 2A:
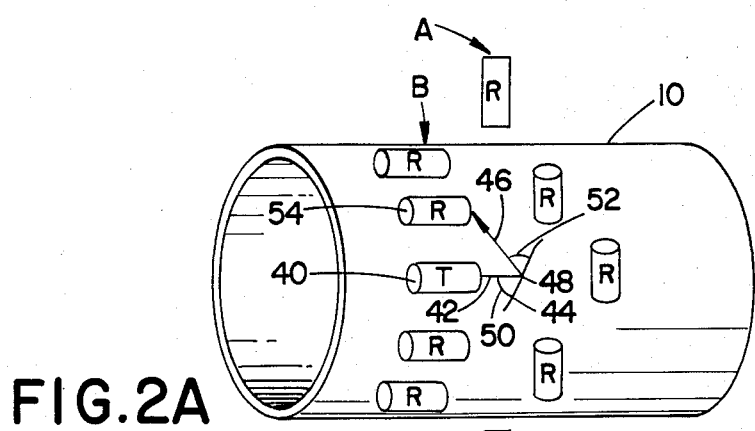
FIGS. 2A, 2B, and 2C illustrate exemplary pulse-echo reflection modes in accordance with the present invention.

With reference to FIG. 2A, one or another preselected number of the transducers in the first and second arrays A, B is triggered to generate an ultrasonic shear wave. As illustrated, one of the axial transducers 40 generates an ultrasonic shear wave 42 propagating axially along the examined object. Upon encountering a crack 44 or other defect, the ultrasonic wave is reflected or echoes and produces a reflected component 46. The transmitting ultrasonic shear wave 42 strikes the crack 44 at a point of intersection 48 at an angle 50, known as the angle of incidence. The reflected component 46 is reflected from the crack at an angle 52, known as the angle of reflection.

The angle of incidence and the angle of reflection are measured relative to a tangent to the point of intersection. In such an interaction, the angle of reflection is equal to the angle of incidence. Thus, the angular orientation of the crack 44 determines the direction in which the reflected component propagates. The reflected component intersects another of the transducers, eg., a transducer 54 of the second array B in the illustration of FIG. 2A. From this information, the point at which the ultrasonic wave struck the crack and the angular orientation of the crack relative to the axial direction are readily determined.

Specifically, it is to be appreciated that a right triangle is defined between the generating transducer 40, the point of intersection 48 with the crack, and the receiving transducer 54. The travel time between transmission of the ultrasonic wave and receipt of the echo component is readily measurable. Further, the velocity of the shear wave is readily determinable by experimental measurement or the like.

These experimental relationships can be described mathematically as follows:

$$d_{42} + d_{46} = V_s t \qquad (1)$$

$$(d_{46})^2 = (d_{42})^2 + (d_t)^2 \qquad (2)$$

where $d_{42}$ is the distance between the transmitting transducer and the crack, $d_{46}$ is the distance between the crack and the receiving transducer, $V_s$ is the velocity of the shear wave, t is the elapsed time between transmission and receipt, and $d_t$ is the distance between the transmitting and receiving transducers. These equations are readily solvable in terms of the distance in the axial direction between the transmitting transducer 40 and the crack:

$$d_{42} = \frac{(V_s t)^2 - (d_t)^2}{V_s t} \quad (3)$$

Similarly, the equal angles of incidence reflection are readily determinable from the quadratic equations:

$$\tan 2\theta = d_t/d_{42} \quad (4)$$

$$2\phi + 2\theta = 180° \quad (5)$$

where $\theta$ is the angle between the surface normal and each of ultrasonic wave 42 and reflected component 46, and $\phi$ is each of the equal angles between the surface tangent and each of the ultrasonic wave 42 and the reflected component 46. These equations are readily solvable for the angle $\phi$ between the defect surface and the direction of propagation and the angle $\theta$ between the surface normal and the direction of propagation:

$$\phi = \frac{180° - \arctan(d_t/d_{42})}{2} \quad (6)$$

$$\theta = \frac{\arctan(d_t/d_{42})}{2} \quad (7)$$

Further, from the intensity of the reflected component, ie., the relative magnitude of the transmitted wave 42 and the reflected component 46, the reflectivity and other physical properties of the defect are determinable.

Figure 2B:
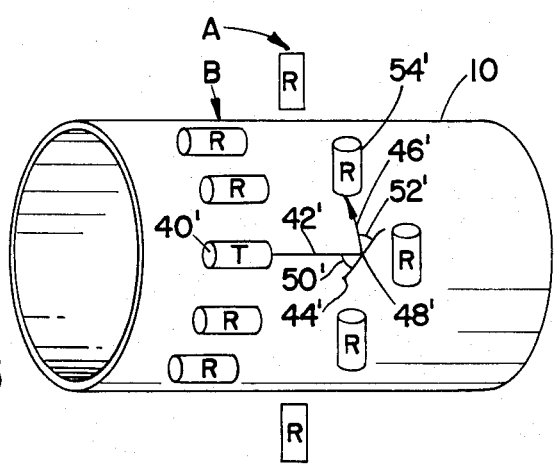

In FIG. 2B, like components to the components of FIG. 2A are identified by the like reference numerals with a primed (') suffix. A transmitting transducer 40' transmits an ultrasonic wave 42' which interacts with a defect 44'. The orientation of the defect surface is such that a reflected component 46' is produced. In the situation of FIG. 2B, the reflected component propagates in a circumferential direction and is received by a receiving transducer 54'. Analogously, the distance in the axial direction from the transmitting transducer to the defect, and the angle of the defect surface relative to the axial direction may both be calculated from the spatial relationship of the transmitting and receiving transducers, the direction of wave propagation, and the wave travel time.

Figure 2C:
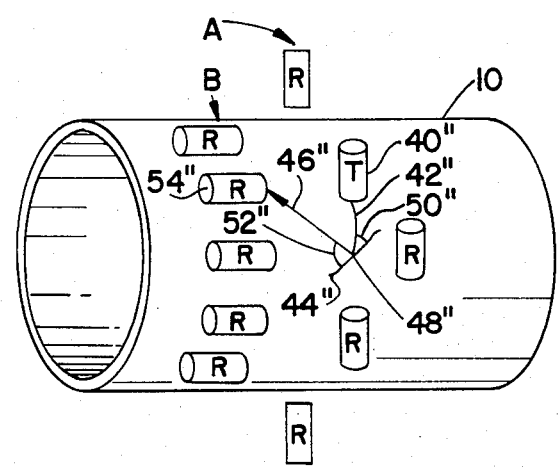

In the showings of FIG. 2C, like components to the components of FIGS. 2A and 2B are identified by like numerals with a double primed ('') suffix. A transmitting transducer 40'' of the circumferential array A generates a circumferential ultrasonc wave 42'' which interacts with a crack 44''. A reflected component 46'' reflects from the crack such that an angle of incidence 56'' equals an angle of reflection 52''. This echo direction results in a receiving transducer 54'' receiving the reflected component and transforming it into an electrical signal. Analogously, the distance of the crack circumferentially from the transmitting transducer and its angular orientation relative to the circumference are readily calculated from the spatial relationship of the transmitting and receiving transducers, and the ultrasonic shear wave travel time.

Figure 3:
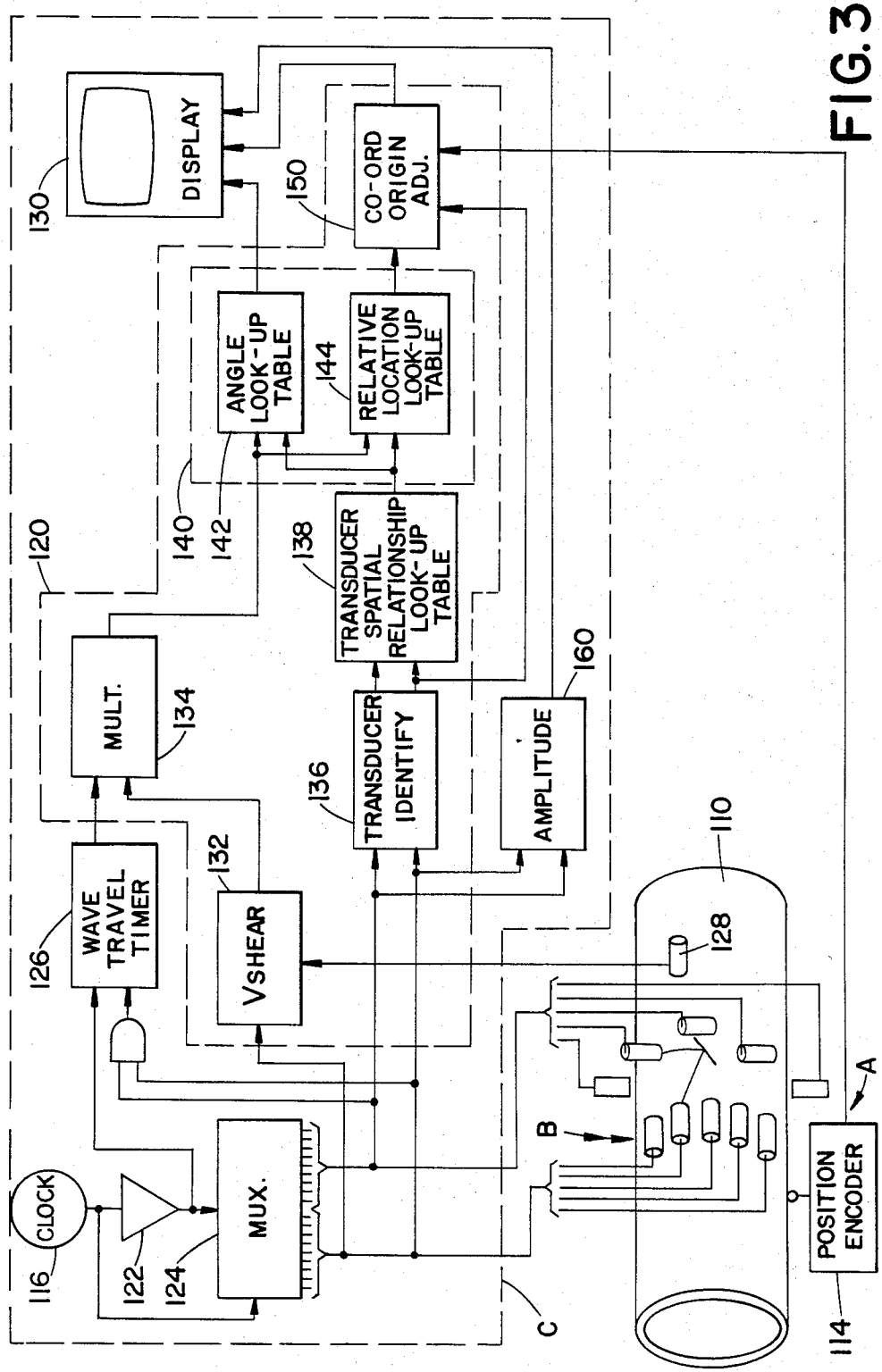
FIG. 3 is a diagrammatic illustration of an alternative defect detecting apparatus in accordance with the present invention.

With reference to FIG. 3, a hard wired circuit is illustrated for controlling the ultrasonic transducers and for determining the location of defects. The first array A is oriented to generate ultrasonic shear waves which propagate circumferentially around a workpiece 110 and the second array B is oriented to generate shear waves axially. A position encoder 114 determines the relative position between the workpiece and the transducer arrays, and a clock 116 periodically generates clocking pulses. A Schmidt trigger or other triggering means 122 converts the clock pulses into firing pulses of the appropriate amplitude and duration for causing one of the ultrasonic transducers to generate an ultrasonic shear wave. A multi-plexing means 124 selectively switches the trigger pulses from the trigger means serially to each individual transducer of the first and second arrays. Each clocking pulse steps the multiplexer such that the trigger pulses are switched serially to each transducer.

An ultrasonic wave travel time measuring means 126 measures the travel time between transmission of an ultrasonic wave and receipt of an ultrasonic reflected component. A location determining means 120 determines the location of a defect for display on a display means 130. In the embodiment of FIG. 3, the location determining means includes an ultrasonic shear wave velocity determining means 132 which determines the velocity of the shear waves along the measured object. As illustrated, the shear wave velocity measuring means measures the travel time over a preselected, known spatial distance. A multiplying means 134 multiplies the wave travel time by the shear wave velocity to determine the total distance traveled by the wave, ie., $d_{42} + d_{46}$. A transducer identifying means 136 is operatively connected with each of the transducers in the first and second arrays to determine which transducer was triggered and which transducer received the reflected component. A transducer spatial relationship determining means 138, such as a look-up table, determines the spatial relationship between the transmitting and echo receiving transducer.

From the spatial relationship of the transmitting and receiving transducers and the wave travel distance, a relative location means 140 determines the distance along the transmission axis between the transmitting transducer and the defect as well as the angle of the defect surface relative to the transmission axis. From the spatial relationship of the transmitting and receiving transducers and the actual wave travel distance, a unique defect location and angle is dictated. An angle look-up table 142 and a relative location look-up table 144 are preprogrammed with the relationships between transducer spatial relationships and wave travel distance. Alternately, the relative location means may be a processor preprogrammed for implementing equations (3) and (6) set forth above, and analogous equations for the other transmitting and receiving transducer combinations.

A coordinate origin adjustment means 150 defines a unique coordinate position on the workpiece relative to a preselected origin point on the work-piece. The origin means 150 includes a position encoder 114 for determining the axial and circumferential position of the examined object 110 relative to the first and second transducer arrays A and B. Specifically, the origin adjustment means compensates for the relative position of the first and second arrays and the examined object, and compensates for the position of the transmitting transducer in the array.

An amplitude detecting means 160 determines the relative amplitude between the transmitted and received pulses. The display means 130 produces a visual display which indicates the location of each defect, the relative reflectivity of the defect surface, the angular orientations of the defect surfaces, and the like.

The invention has been described with reference to the preferred and alternate embodiments. Obviously, modifications and alterations will occur to others upon reading and understanding this specification. It is intended to include all such modifications and alterations insofar as they come within the scope of the appended claims or the equivalents thereof.

Having thus described the invention, it is now claimed:

1. A method of ultrasonically locating defects in an examined object with a first transducer array including a plurality of transducers for generating ultrasonic shear waves along the examined object in a first transmission direction and for receiving reflected ultrasonic wave components from the examined object and a second transducer array for transmitting ultrasonic shear waves along the examined object in a second transmission direction and receiving reflected ultrasonic wave components from the examined object, the method comprising:

(a) actuating at least one transducer of the first and second arrays to transmit an ultrasonic shear wave along the examined object and causing the remaining transducers of the first and second arrays to assume a reflected component receiving mode;

(b) measuring an ultrasonic wave travel time between transmission of an ultrasonic wave by a transmitting transducer and receipt of a reflected component by a receiving transducer;

(c) determining the spatial relationship between the transmitting transducer and the receiving transducer;

(d) determining the location of the defect flaw from the measured travel time and the relative spatial relationship of the transmitting and receiving transducers; and, (e) repeating steps (a)-(d) with other transducers of the first and second arrays.

2. The method as set forth in claim 1 further including the step of determining the angular orientation of the defect relative to the transmission direction of each transmitted ultrasonic wave.

3. The method as set forth in claim 1 further including measuring the amplitude of the reflected component relative to the amplitude of the transmitted ultrasonic wave.

4. The method as set forth in claim 1 wherein a single transducer is actuated at a time to function as the transmitting transducer.

5. The method as set forth in claim 1 wherein the examined object is generally cylindrical, the first transmission direction being circumferentially of said object and the second transmission direction being axially along said object.

6. The method as set forth in claim 1 wherein the step of determining the location of the defect includes determining the shear wave velocity of ultrasonic shear waves in traversing the examined object.

7. The method as set forth in claim 6 wherein the step of determining the defect location further includes multiplying the measured travel time by the determined shear wave velocity to determine the distance which the ultrasonic wave traveled from the transmitting transducer to the defect and to the receiving transducer.

8. The method as set forth in claim 7 wherein the defect location determining step further includes (1) determining the relative position between the first and second arrays and a preselected origin on the examined object, (2) determining the spatial relationship of each transmitting transducer and the first and second arrays, and (3) determining a position of the defect relative to the preselected origin.

9. An ultrasonic inspection apparatus for locating defects in an examined object, the apparatus comprising:

a first transducer array including a plurality of first ultrasonic transducers, each first ultrasonic transducer transmitting in response to a trigger signal an ultrasonic shear wave which travels in a first direction along the examined object and producing an echo signal in response to receiving a reflected ultrasonic component;

a second transducer array including a plurality of second ultrasonic transducers, each second ultrasonic transducer transmitting in response to a trigger signal an ultrasonic shear wave which travels in a second direction along the examined object and producing an echo signal in response to receiving a reflected ultrasonic component;

multiplexer means for selectively switching trigger pulses to preselected transmitting transducers of the first and second arrays;

travel time measuring means for measuring time between transmission of an ultrasonic wave by the transmitting transducer and receipt of a reflected component by a receiving transducer, the travel time measuring means being operatively connected with the first and second ultrasonic transducer arrays;

location determining means operatively connected with the travel time measuring means and the first and second ultrasonic transducer arrays for determining the location of a reflective defect from the measured travel time and the spatial relationship of the transmitting and receiving transducers.

10. The inspection apparatus as set forth in claim 9 further including defect orientation determining means for determining an angular orientation of a defect surface from the determined defect location and the spatial relationship of the transmitting and receiving ultrasonic transducers.

11. The inspection apparatus as set forth in claim 9 further including reflected component amplitude measuring means for measuring the amplitude of the received reflected component.

12. The inspection apparatus as set forth in claim 9 wherein the first direction is substantially perpendicular to the second direction.

13. The inspection apparatus as set forth in claim 12 wherein the examined object is generally cylindrical with the first direction being circumferentially around the object and the second direction being axially along the object.

14. The inspection apparatus as set forth in claim 9 wherein the location determining means includes shear wave velocity determining means for determining the velocity of ultrasonic shear waves traversing the examined object.

15. The inspection apparatus as set forth in claim 14 wherein the location determining means includes multiplying means for multiplying the measured travel time by the determined shear wave velocity to determine the distance which the ultrasonic wave traveled from the transmitting transducer to a defect and to the receiving transducer.

16. The inspection apparatus as set forth in claim 15 wherein the location determining means includes relative location means for determining the location of the defect relative to the transmitting transducer and origin means for adjusting the relative location for the spatial relationship of the transmitting transducer relative to a preselected point of origin on the examined object.

* * * * *